(12) United States Patent
Jacobson et al.

(10) Patent No.: US 11,666,293 B2
(45) Date of Patent: Jun. 6, 2023

(54) EXTENDED FIELD-OF-VIEW X-RAY IMAGING USING MULTIPLE X-RAY SOURCES AND ONE OR MORE LATERALLY OFFSET X-RAY DETECTORS

(71) Applicants: THE BRIGHAM AND WOMEN'S HOSPITAL, INC., Boston, MA (US); DANA-FARBER CANCER INSTITUTE, INC., Boston, MA (US)

(72) Inventors: Matthew Jacobson, Natlick, MA (US); Ross Berbeco, Cambridge, MA (US)

(73) Assignees: THE BRIGHAM AND WOMEN'S HOSPITAL, INC., Boston, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 17/368,539

(22) Filed: Jul. 6, 2021

(65) Prior Publication Data

US 2022/0000436 A1 Jan. 6, 2022

Related U.S. Application Data

(60) Provisional application No. 63/136,622, filed on Jan. 12, 2021, provisional application No. 63/047,937, filed on Jul. 3, 2020.

(51) Int. Cl.
*A61B 6/00* (2006.01)
*A61B 6/03* (2006.01)
(Continued)

(52) U.S. Cl.
CPC ............ *A61B 6/4014* (2013.01); *A61B 6/032* (2013.01); *A61B 6/4085* (2013.01);
(Continued)

(58) Field of Classification Search
CPC ..... A61B 6/4014; A61B 6/032; A61B 6/4085; A61B 6/4435; A61B 6/5258; A61B 6/482;
(Continued)

(56) References Cited

U.S. PATENT DOCUMENTS

| 7,108,421 B2* | 9/2006 | Gregerson | A61B 6/4021 378/146 |
| 7,324,623 B2* | 1/2008 | Heuscher | A61B 6/4014 378/19 |

(Continued)

FOREIGN PATENT DOCUMENTS

EP 3499272 A1 * 6/2019 ............... G01T 1/20

OTHER PUBLICATIONS

Joemai et al., "Metal artifact reduction for CT:Development, implementation, and clinical comparision of a generic and a scanner-specific technique", Medical Physics, vol. 39, No. 2, pp. 1125-1132. (Year: 2012).*

(Continued)

*Primary Examiner* — Kiho Kim
(74) *Attorney, Agent, or Firm* — Quarles & Brady LLP

(57) ABSTRACT

Extended field-of-view imaging is enabled by combined imaging with a kilovolt ("kV") x-ray source and a megavolt ("MV") x-ray source, in which at least one of the corresponding x-ray detectors is laterally offset from the target isocenter by an amount such that the x-ray detector does not have a view of the target isocenter. This scan geometry enables the reconstruction of non-truncated images without resorting to the more expensive solution of outfitting the imaging or radiotherapy system with enlarged x-ray detectors.

26 Claims, 6 Drawing Sheets

(51) Int. Cl.
  *A61N 5/10* (2006.01)
  *G06T 11/00* (2006.01)
  *G01T 1/20* (2006.01)
  *G01T 1/202* (2006.01)

(52) U.S. Cl.
  CPC .......... *A61B 6/4435* (2013.01); *A61B 6/5258* (2013.01); *A61N 5/1071* (2013.01); *A61N 5/1081* (2013.01); *G01T 1/2018* (2013.01); *G01T 1/2023* (2013.01); *G06T 11/006* (2013.01); *A61N 2005/1061* (2013.01); *G06T 2211/408* (2013.01)

(58) Field of Classification Search
  CPC ................ A61N 5/1071; A61N 5/1081; A61N 2005/1061; A61N 5/1049; G01T 1/2018; G01T 1/2023; G06T 11/006; G06T 2211/408
  See application file for complete search history.

(56) References Cited

U.S. PATENT DOCUMENTS

| | | | |
|---|---|---|---|
| 7,460,636 B2 * | 12/2008 | Ein-Gal | A61B 6/4014 378/19 |
| 10,080,538 B2 | 9/2018 | Hofmann | |
| 10,121,267 B2 | 11/2018 | Lin | |
| 10,485,496 B2 | 11/2019 | Goleti Venkata | |
| 2008/0011960 A1 * | 1/2008 | Yorkston | G21K 4/00 250/370.09 |
| 2016/0278719 A1 | 9/2016 | Jensen | |
| 2020/0030634 A1 | 1/2020 | Van Heteren | |
| 2020/0170590 A1 * | 6/2020 | Gagnon | A61B 6/545 |
| 2021/0080597 A1 * | 3/2021 | Wimmers | G01T 1/2002 |

OTHER PUBLICATIONS

Ichikawa et al., "A three-dimensional cross-directional bilateral filter for edge-preserving noise reduction of low-dose computed tomography images", Computers in Biology and Medicine, vol. 111, No. 103353, p. 1-9. (Year: 2019).*

Chueh et al., "Development of novel statistical reconstruction algorithms for poly-energetic X-ray computed tomography", Computer Methods and Programs in Biomedicine, vol. 92, pp. 289-293. (Year: 2008).*

Stayman et al., "PIRPLE: a penalized-likelihood framework for incorporation of prior images in CT reconstruction", Physics in Medicine and Biology, vol. 58, pp. 7563-7582. (Year: 2013).*

* cited by examiner

EXTENDED FIELD-OF-VIEW X-RAY IMAGING USING MULTIPLE X-RAY SOURCES AND ONE OR MORE LATERALLY OFFSET X-RAY DETECTORS

CROSS-REFERENCE TO RELATED APPLICATIONS

This application claims the benefit of U.S. Provisional Patent Application Ser. No. 63/047,937 filed on Jul. 3, 2020, and entitled "SYSTEM FOR AND METHOD OF COMBINING DATA FROM MULTIPLE X-RAY IMAGERS OF AN EXTERNAL BEAM RADIOTHERAPY SYSTEM TO ACHIEVE LARGE FIELD OF VIEW ON-TREATMENT CONE BEAM CT IMAGES," and U.S. Provisional Patent Application Ser. No. 63/136,622 filed on Jan. 12, 2021, and entitled "SYSTEM FOR AND METHOD OF ARTIFACT REDUCTION IN AN EXTERNAL BEAM RADIOTHERAPY SYSTEM," both of which are herein incorporated by reference in their entirety.

BACKGROUND

In external beam radiotherapy (EBRT), on-treatment cone beam CT (CBCT) with a single, traditionally sized detector gives a limited field of view (FOV) diameter. This often results in undesirably truncated images of large patient anatomy.

SUMMARY OF THE DISCLOSURE

The present disclosure addresses the aforementioned drawbacks by providing an imaging system that includes a gantry that is rotatably coupled to a drive stand and is configured to rotate through an imaging arc about a bore. A first x-ray source is mounted on the gantry and configured to direct x-rays of a first beam energy through a peripheral portion of a target volume disposed in the bore and toward a first x-ray detector mounted on the gantry laterally offset from the center of the target volume. A second x-ray source is also mounted on the gantry angularly offset from the first x-ray source and configured to direct x-rays of a second beam energy higher than the first beam energy through a portion of the target volume including the center of the target volume and toward a second x-ray detector mounted on the gantry. A processor is configured to: cause the gantry to perform a rotation including an imaging arc; receive first x-ray measurement data from the first x-ray detector; receive second x-ray measurement data from the second x-ray detector; and reconstruct an image of the target volume from the first and second x-ray measurement data, wherein the image has an extended field-of-view.

It is another aspect of the present disclosure to provide a computer-implemented method of imaging in an imaging system that includes a gantry that is configured to rotate in an imaging arc about a bore, a first x-ray source mounted on the gantry and configured to direct x-rays of a first beam energy through a peripheral portion of a target volume disposed in the bore and toward a first x-ray detector mounted on the gantry laterally offset from the center of the target volume, and a second x-ray source mounted on the gantry angularly offset from the first x-ray source and configured to direct x-rays of a second beam energy higher than the first energy through a portion of the target volume including the center of the target volume and toward a second x-ray detector mounted on the gantry. The method includes receiving first x-ray measurement data from the first x-ray detector while the gantry is rotating through the imaging arc; receiving second x-ray measurement data from the second x-ray detector while the gantry is rotating through the imaging arc; and reconstructing an image of the target volume from the first and second x-ray measurement data using a computer system, wherein the image depicts an extended field-of-view region.

It is still another aspect of the present disclosure to provide a method of reconstructing an image from x-ray measurement data. First x-ray measurement data are accessed with a computer system, where the first x-ray measurement data correspond to a first x-ray beam having a first x-ray beam energy passing through a peripheral portion of a target volume along a beam axis that is laterally offset from a center of the target volume. Second x-ray measurement data are also accessed with the computer system, where the second x-ray measurement data correspond to a second x-ray beam having a second x-ray beam energy higher than the first x-ray beam energy and passing through a portion of the target volume including the center of the target volume. The first x-ray measurement data and the second x-ray measurement data are converted to monoenergetic projection data corresponding to a common x-ray beam energy using the computer system. An image is reconstructed from the monoenergetic projection data with the computer system, where the image depicts an extended field-of-view of the target volume.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
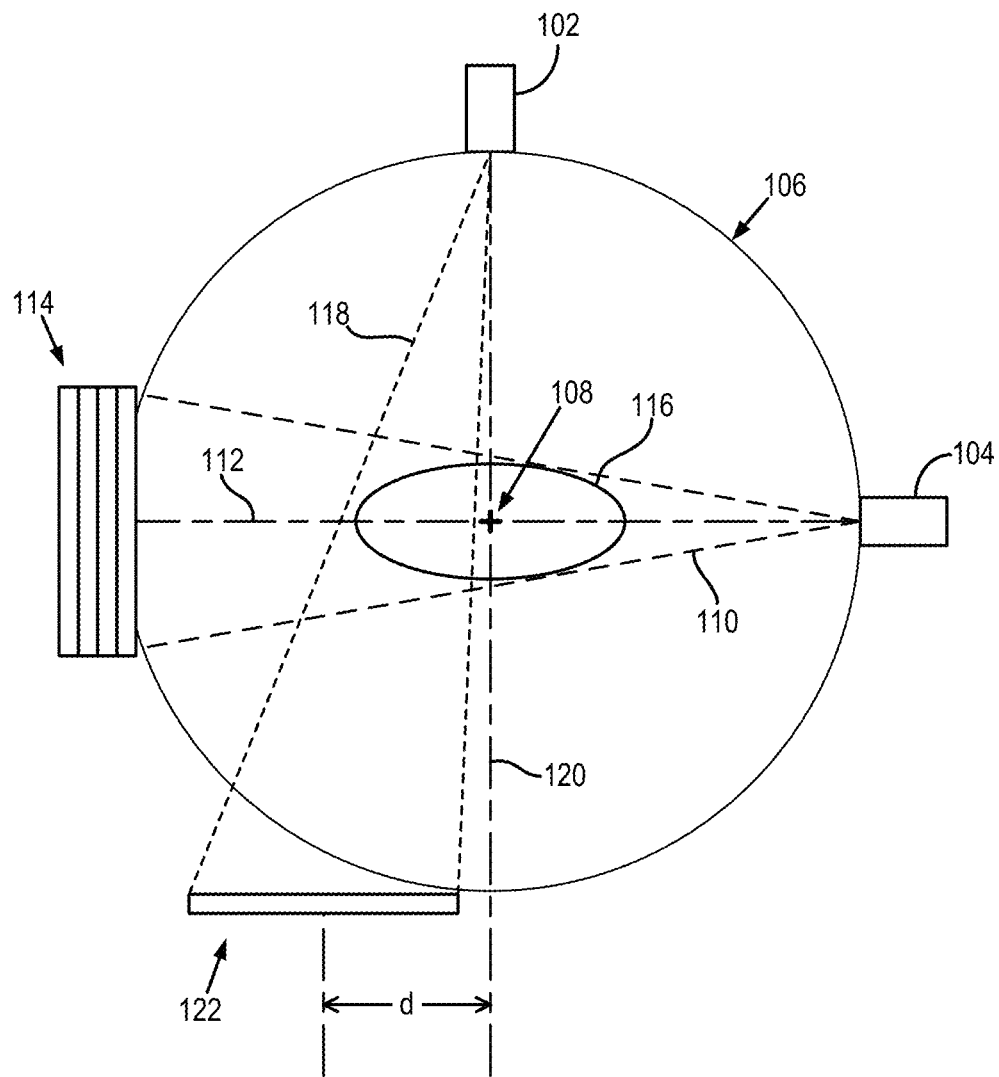
FIG. 1 shows an example scan geometry implementing two x-ray sources and at least one laterally offset x-ray detector.

Described here are systems and methods for x-ray imaging and/or image guided radiotherapy, in which imaging is provided using a kilovolt ("kV") x-ray source and a megavolt ("MV") x-ray source in combination, and in which at least one of the x-ray detectors is laterally offset from the target isocenter by an amount such that the x-ray detector does not have a view of the target isocenter. As a result, the systems and methods described in the present disclosure implement a scan geometry that combines measurements from one or more laterally offset detectors to cover a large field-of-view ("FOV") diameter. Advantageously, this scan geometry enables the reconstruction of non-truncated images without resorting to the more expensive solution of outfitting the radiotherapy system with enlarged x-ray detectors.

In an example configuration, the detector corresponding to the kV x-ray source can be laterally offset from the target isocenter, and the detector corresponding to the MV x-ray source can be centered with respect to the target isocenter. Additionally, in some embodiments the detector corresponding to the MV x-ray source can be a multilayer x-ray detector. Advantageously, the systems and methods described in the present disclosure are capable of imaging larger FOVs by combining x-ray data from the kV x-ray source (e.g., a kV-CBCT imager) and the MV x-ray source (e.g., a LINAC MV-imager) found on conventional external beam radiotherapy ("EBRT") systems. As noted above, this allows for non-truncated images to be obtained without having to outfit the EBRT system with enlarged x-ray detectors.

It is another aspect of the present disclosure to provide systems and methods for reconstructing images from data acquired using the combined kV and MV x-ray sources using the scan geometry described herein. In general, the image reconstruction when using a combination of kV and MV x-ray sources should account for the differences in energy spectra. Advantageously, the image reconstruction techniques described in the present disclosure enable both correcting for differences in energy spectra between the two x-ray sources and reducing noise content in the x-ray measurements (e.g., the higher noise level of the MV imager data).

The systems and methods described in the present disclosure can advantageously enable adaptive radiotherapy ("ART") practices in radiation oncology treatment centers. For example, the wide FOV images generated using the systems and methods described herein allow more accurate three-dimensional ("3D") dose map calculations than with traditional, truncated CBCT images. This in turn allows for adaptive changes to treatment plans to be guided by on-treatment x-ray data.

In some instances, it can be advantageous to combine x-ray measurement data from kV and MV sources without extending the FOV using a laterally offset x-ray detector. For example, by combining the kV and MV x-ray measurement data using the techniques described in the present disclosure, additional benefits can be realized. As a non-limiting example, metal artifact reduction can be implemented when combining, or after combining, the kV and MV x-ray measurement data.

Referring now to FIG. 1, an example scan geometry that can be implemented using the techniques described in the present disclosure is illustrated. In this example, the EBRT system includes a kV x-ray source 102 and an MV x-ray source 104. The kV x-ray source 102 and the MV x-ray source 104 are coupled to a gantry 106 such that they can be rotated, collectively or independently, about an isocenter 108. Alternatively, the kV x-ray source 102 and the MV x-ray source 104 may be coupled to one or more support arms that are rotatable about the isocenter 108, or may be housed in one or more housings that are rotatable about the isocenter 108.

As shown, the MV x-ray source 104 generates an MV x-ray beam 110 that is directed along an x-ray source axis 112 that is centered on the isocenter 108. The MV x-ray beam 110 impinges upon a first x-ray detector 114 after passing through a target 116, which may be a patient or a portion of a patient, an imaging phantom, or so on. The kV x-ray source 104 generates a kV x-ray beam 118 that is directed along a direction that is angled away, or otherwise offset, from a central axis that extends through the target isocenter 108, such that the kV x-ray beam 118 is laterally offset from the isocenter 108. The kV x-ray beam 118 impinges upon a second x-ray detector 122 after passing through the target 116. In general, the kV x-ray beam 118 is laterally offset from the isocenter 108 by an amount, d, such that the second x-ray detector 122 does not have a view of the isocenter 108.

As a non-limiting example, the second x-ray detector 122 can be offset from the isocenter 108 by an amount in the range of several centimeters to tens of centimeters. For instance, the second x-ray detector 122 can be offset from the isocenter 108 by an amount in the range of 10-50 cm. As another example, the second x-ray detector 122 can be offset from the isocenter 108 by an amount in the range of 25-40 cm, such as 32 cm.

In a non-limiting example, the second x-ray detector 122 can include a single layer detector and the first x-ray detector 114 can include a multilayer x-ray detector. The multilayer x-ray detector can be composed of multiple layers that contain scintillator sublayers and/or photodiode sublayers. As an example, each layer in the multilayer detector can include a scintillator sublayer and a photodiode sublayer.

In one configuration, each scintillator sublayer can be composed of $GdO_2S_2$:Tb or other suitable scintillators, and may have a submillimeter thickness. For instance, each scintillator sublayer may have a thickness less than 1 mm, and may be in a range of 0.3-0.7 mm. As a non-limiting example, the scintillator sublayer may have a thickness in the range of 0.500-0.550 mm, such as 0.506 mm. In one configuration, each photodiode sublayer can be composed of Si:H or other suitable photodiodes, and may have a submillimeter thickness. For instance, each photodiode sublayer may have a thickness less than 1 mm, and may be in a range of 0.5-0.9 mm. As a non-limiting example, the photodiode sublayer may have a thickness of 0.7 mm. The multilayer detector may, as one non-limiting example, be composed of four layers, with each layer being composed of a single scintillator sublayer and a single photodiode sublayer. Such a multilayered detector configuration enables an increase in detection efficiency.

As a non-limiting example, the systems and methods described in the present disclosure can implement an acquisition geometry in which the MV x-ray source 104 generates a 2.5 MV x-ray beam 110 that impinges upon the first x-ray detector 114, which includes a 43 cm multilayer detector, and in which the kV x-ray source 102 generates a 125 kVp x-ray beam 118 that impinges upon the second x-ray detector 122, which includes a 40 cm kV detector with a 32 cm lateral offset. In this configuration, the MV x-ray source 104 scans the central region of the target 116 and the kV x-ray source 102 scans the periphery of the target 116. As a result of this acquisition geometry, a 65 cm FOV is attainable.

Figure 2:
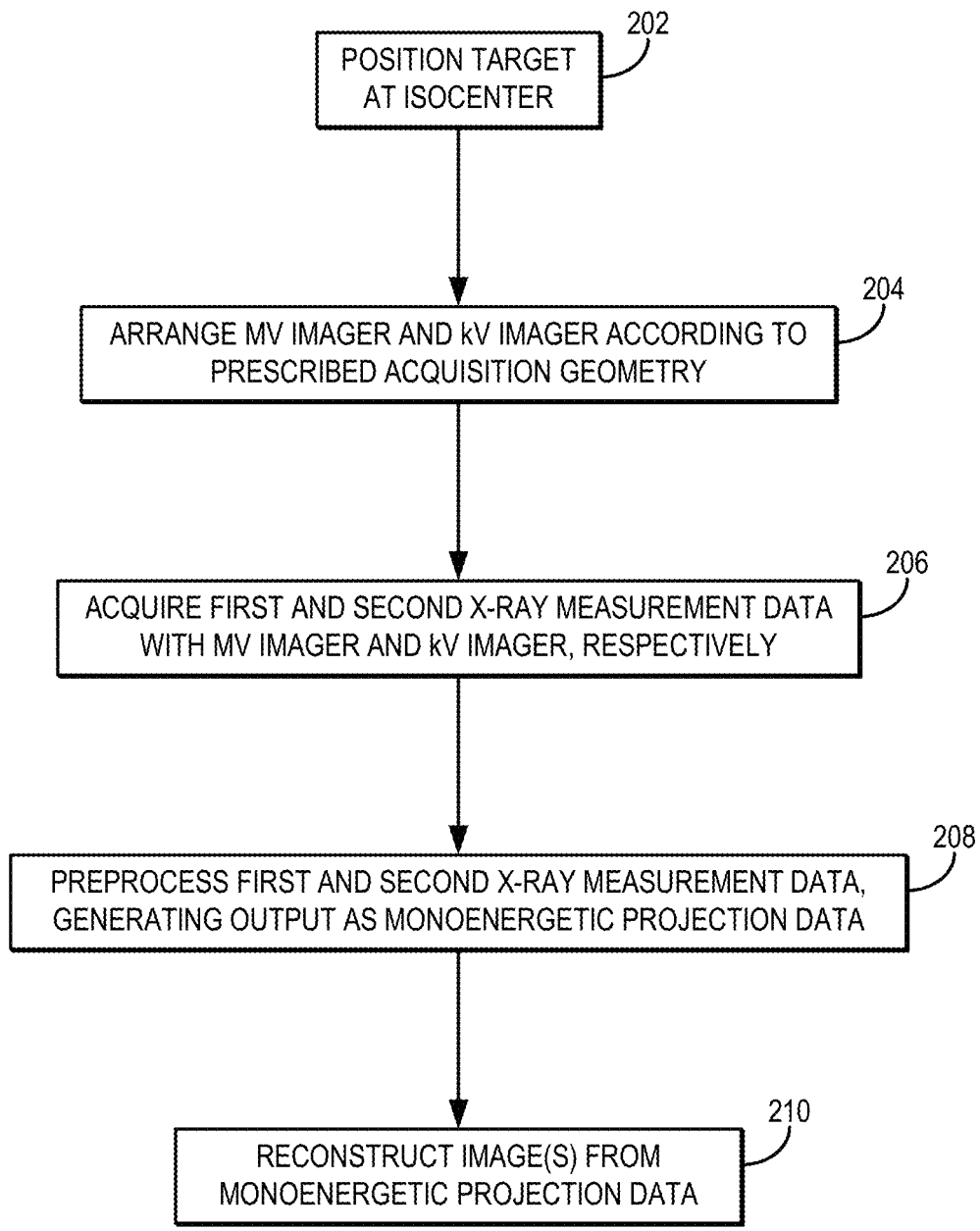
FIG. 2 is a flowchart setting forth the steps of an example method for imaging a target volume using the scan geometries described in the present disclosure.

Referring now to FIG. 2, a flowchart is illustrated as setting forth the steps of an example method for acquiring x-ray measurement data using a combined MV x-ray source and laterally offset kV x-ray source, and reconstructing images therefrom. The method includes positioning a target at an isocenter of an EBRT system, as indicated at step 202. The target may be a patient or an object, such as an imaging phantom or a quality assurance ("QA") phantom.

An MV imager and a kV imager of the EBRT system are then arranged about the target using a prescribed acquisition geometry, as indicated at step 204. For example, the MV imager is arranged to be centered along an axis extending through the isocenter and the kV imager is arranged to be laterally offset from the target isocenter by an amount such that the kV imager does not have a view of the isocenter. In this way, an extended FOV can be achieved, as described above. Alternatively, both the MV imager and the kV imager can be centered on respective axes that each pass through the isocenter. In this latter configuration the extended FOV achieved by laterally offsetting the kV imager may not be realized. In some implementations, an extended kV detector can be implemented to achieve an extended FOV.

First x-ray measurement data and second x-ray measurement data are then acquired using the MV imager and kV imager, respectively, as indicated at step 206. In this instance, the first x-ray measurement data include data acquired at a first energy spectra corresponding to the MV x-ray source and the second x-ray measurement data include data acquired at a second energy spectra corresponding to the kV x-ray source. The first and second x-ray measurement data can be obtained simultaneously by simultaneously generating both an MV x-ray beam and a kV x-ray beam. Additionally or alternatively, the first and second x-ray measurement data can be obtained sequentially or in another arbitrary interleaved manner by switching between generating the MV x-ray beam and the kV x-ray beam.

The first and second x-ray measurement data are acquired while moving the MV imager and kV imager to different positions about the target. For instance, the MV imager and kV imager can be rotated through a plurality of different rotation angles (e.g., gantry angles, or the like) about the target. Additionally or alternatively, the MV imager and/or kV imager may also be translated along one or more directions while acquiring the respective x-ray measurement data. Additionally or alternatively, the target can be moved relative to the MV imager and/or kV imager in order to obtain different views of the target.

As described above, the MV imager is aligned to be centered on the isocenter while the kV imager is laterally offset from the isocenter by an amount such that the kV imager does not have a view of the isocenter. In this way, the first x-ray measurement data will include views of the central region of the target whereas the second x-ray measurement data will include views of the periphery of the target.

The first and second x-ray measurement data are then preprocessed by a computer system, generating output as monoenergetic projection data, as indicated at step 208. For instance, the first and/or second x-ray measurement data can be processed to remove or otherwise reduce image noise. As a non-limiting example, the first and/or second x-ray measurement data can be processed using an edge-preserving algorithm in order to mitigate image noise. Additionally or alternatively, the first and/or second x-ray measurement data can be processed using a poly-energetic correction technique to account for the different energy spectra over which the first and second x-ray measurement data were acquired.

Figure 3:
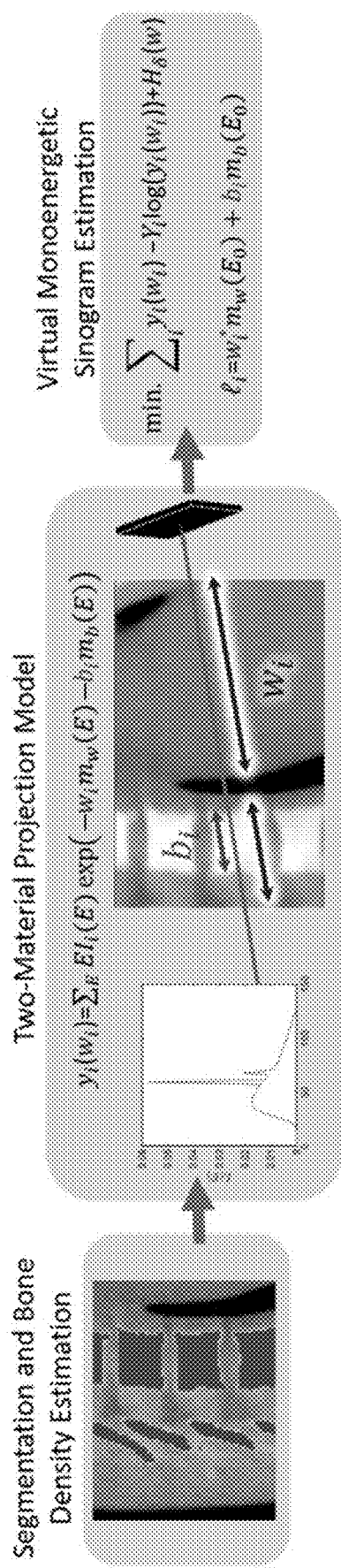
FIG. 3 illustrates an example mono-energizing transform for converting kV-energy and MV-energy x-ray measurements to monoenergetic projection data corresponding to a common energy level.

As an example, a mono-energizing sinogram transform can be implemented. As shown in FIG. 3, segmentation and bone density estimation can be performed prior to implementing a two-material projection model. The algorithm estimates the 3D density distribution of bone and its projections $b_i$ from an initial reconstruction, such as an initial water-corrected FDK reconstruction. Using the known source spectrum, the contribution of water to the projections can then be estimated and used to transform measurements from both imagers to monoenergetic virtual projections, such as 70 keV virtual monoenergetic projections. As noted above, an edge-preserving algorithm can also be incorporated into this poly-energetic correction technique. For example, edge-preserving Huber roughness penalties can be incorporated in order to improve noise suppression. As shown in FIG. 3. a Poisson loglikelihood optimization problem can be solved with an edge-preserving Huber roughness penalty $H_\delta(w)$. The solution gives the density projections, $w_i$, of water along the i-th measured ray. This allows virtual monoenergetic projections $\ell_i$ to be formed at a nominal energy $E_0$=70 keV and reconstructed.

One or more images are then reconstructed from the preprocessed first and second x-ray measurement data, as indicated at step 210. For example, the first and second x-ray measurement data can be converted to monoenergetic projection data as described above, and one or more images can be reconstructed from the monoenergetic projection data. As a non-limiting example, one or more images can be generated from the monoenergetic projection data using an FDK reconstruction to obtain the final CBCT image(s). By combining kV and MV data in this way, reconstructing non-truncated on-treatment CBCT images is achievable with significant soft tissue differentiation performance and at clinically applicable doses.

Figure 4:
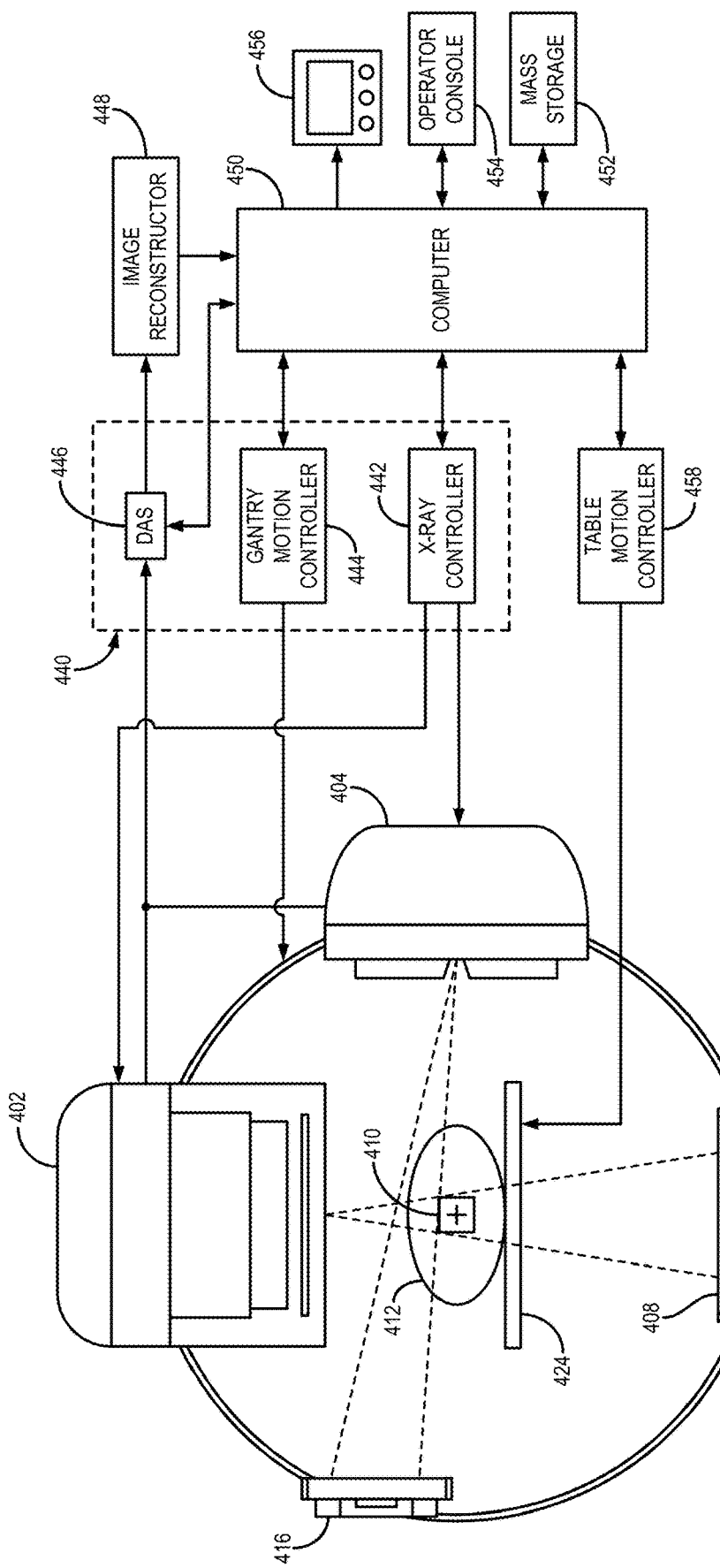
FIG. 4 is a block diagram of an example external beam radiotherapy ("EBRT") system incorporating a kV x-ray source and an MV x-ray source arranged according to the scan geometries described in the present disclosure.

Referring to FIG. 4, an example image-guided radiation therapy ("IGRT") system 400 includes a therapeutic x-ray source 402 and a diagnostic x-ray source 404. The therapeutic x-ray source 402 can include an x-ray source configured to generate x-rays in an MV energy spectra and, thus, may be an MV x-ray source. In addition to generating the treatment beam, the therapeutic x-ray source 402 can produce an MV x-ray beam for imaging that is directed toward a first detector 408. The diagnostic x-ray source 404 projects a cone-beam of x-rays toward a second detector 416. The diagnostic x-ray source 404 can include an x-ray source configured to generate x-rays in a kV energy spectra and, thus, may be a kV x-ray source.

In some configurations, both the therapeutic x-ray source 402 and diagnostic x-ray source 404 can be coupled to a rotatable gantry 406 that rotates about a pivot axis through an imaging arc about a bore. The rotatable gantry 406 can be, for example, rotatably coupled to a drive stand. The rotatable gantry 406 allows either of the x-ray sources, 402 and 404, to be aligned in a desired manner with respect to a target volume 410 in a subject 412 positioned on a patient table 424. Alternatively, the therapeutic x-ray source 402 and diagnostic x-ray source 404 can be coupled to different rotatable gantries, or to different moveable supports (e.g., articulating support arms), such that the therapeutic x-ray source 402 and diagnostic x-ray source 404 can be moved independently of each other in a desired scan configuration.

In some configurations, the first detector 408 may be a multilayer detector, as described above. As an example, the second detector 416 may be formed by a number of detector elements that together sense the projected x-rays that pass through the subject 412. Each detector element produces an electrical signal that represents the intensity of an impinging x-ray beam and, hence, the attenuation of the beam as it passes through the subject 412.

The rotation of the rotatable gantry 406 and the operation of the x-ray sources, 402 and 404, are governed by a control mechanism 440 of the IGRT system. The control mechanism 440 includes an x-ray controller 442 that provides power and timing signals to the x-ray sources, 402 and 404, and a gantry motor controller 444 that controls the rotational speed and position of the gantry 406. A data acquisition system ("DAS") 446 in the control mechanism 440 samples analog data from detector elements and converts the data to digital signals for subsequent processing. An image reconstructor 448, receives sampled and digitized x-ray data from the DAS 446 and performs high speed image reconstruction according to the techniques described in the present disclosure. The reconstructed image is applied as an input to a computer 450 which stores the image in a mass storage device 452.

The computer 450 also receives commands and scanning parameters from an operator via a console 454 that has a keyboard. An associated display 456 allows the operator to observe the reconstructed image and other data from the computer 450. The operator supplied commands and parameters are used by the computer 450 to provide control signals and information to the DAS 446, the x-ray controller 442 and the gantry motor controller 444. In addition, the computer 450 operates a table motor controller 458 which controls the motorized patient table 424 to position the subject 412 within the gantry 406.

Figure 5A:
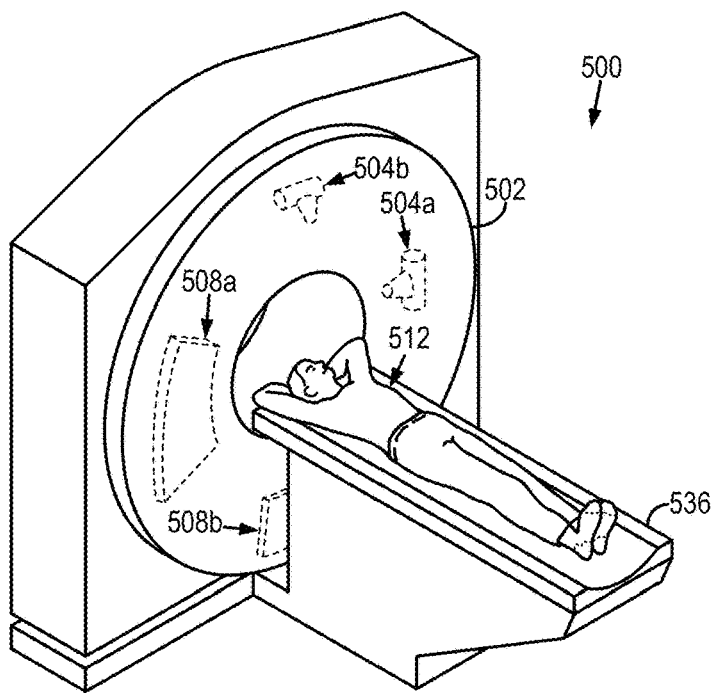
FIGS. 5A and 5B depict an example computed tomography ("CT") imaging system that can implement the scan geometries and imaging techniques described in the present disclosure.
Figure 5B:
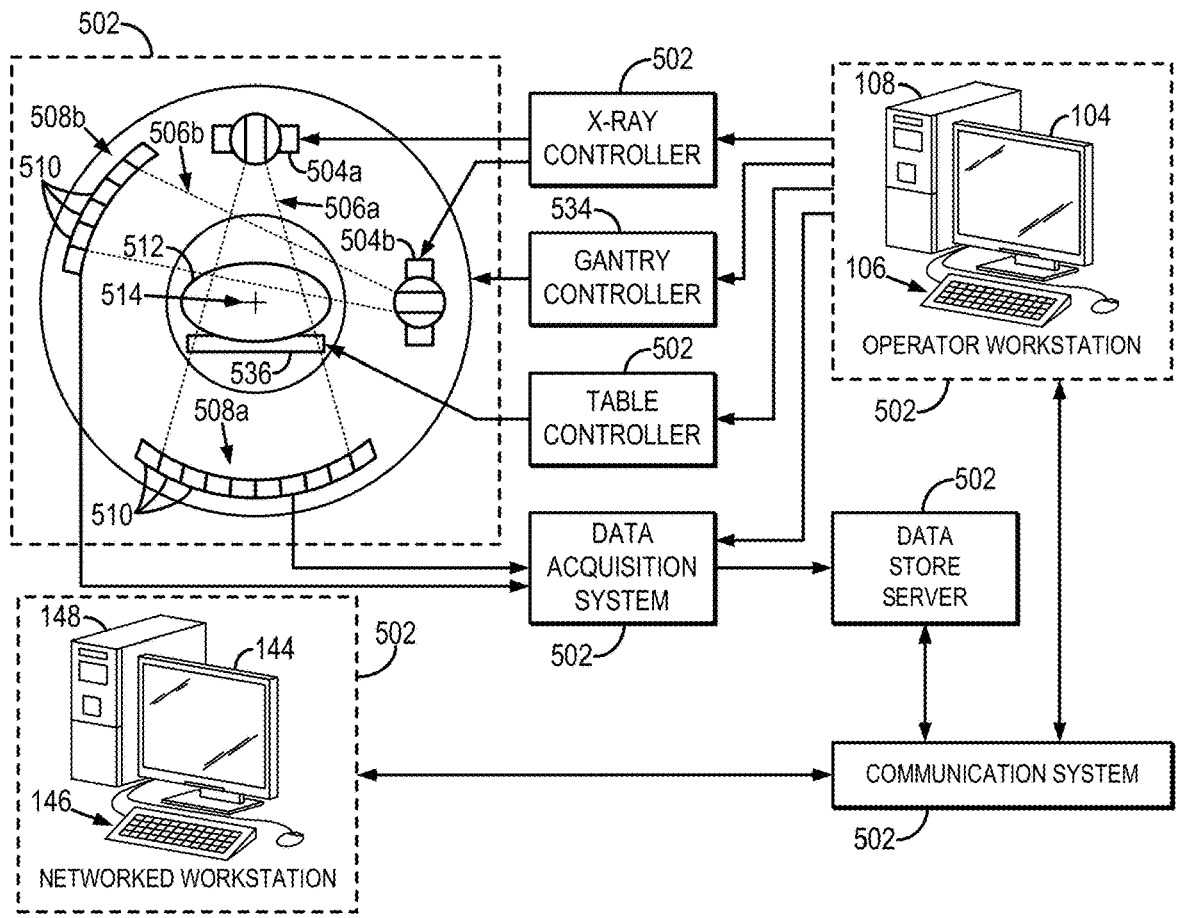

In some implementations, the systems and methods described in the present disclosure can be integrated into a computed tomography ("CT") imaging system. Referring particularly now to FIGS. 5A and 5B, an example of an x-ray CT imaging system 500 is illustrated. The CT system includes a gantry 502, to which two x-ray sources 504a, 504b are coupled. The first x-ray source 504a projects a first x-ray beam 506a, which may be a fan-beam or cone-beam of x-rays, at a first beam energy towards a first detector array 508a on the opposite side of the gantry 502. Likewise, the second x-ray source 504b projects a second x-ray beam 506b, which may be a fan-beam or cone-beam of x-rays, at a second beam energy towards a second detector array 508b on the opposite side of the gantry 502. As described above, at least one of the x-ray sources 506 and corresponding detector arrays 508 are arranged such that the detector array 508 is laterally offset from the target isocenter.

Each detector array 508 includes a number of x-ray detector elements 510. Together, the x-ray detector elements 510 sense the projected x-rays 506 that pass through a subject 512, such as a medical patient or an object undergoing examination, that is positioned in the CT system 500. Each x-ray detector element 510 produces an electrical signal that may represent the intensity of an impinging x-ray beam and, hence, the attenuation of the beam as it passes through the subject 512. In some configurations, each x-ray detector 510 is capable of counting the number of x-ray photons that impinge upon the detector 510. During a scan to acquire x-ray projection data, the gantry 502 and the components mounted thereon rotate about a center of rotation 514 located within the CT system 500.

The CT system 500 also includes an operator workstation 516, which typically includes a display 518; one or more input devices 520, such as a keyboard and mouse; and a computer processor 522. The computer processor 522 may include a commercially available programmable machine running a commercially available operating system. The operator workstation 516 provides the operator interface that enables scanning control parameters to be entered into the CT system 500. In general, the operator workstation 516 is in communication with a data store server 524 and an image reconstruction system 526. By way of example, the operator workstation 516, data store sever 524, and image reconstruction system 526 may be connected via a communication system 528, which may include any suitable network connection, whether wired, wireless, or a combination of both. As an example, the communication system 528 may include both proprietary or dedicated networks, as well as open networks, such as the internet.

The operator workstation 516 is also in communication with a control system 530 that controls operation of the CT system 500. The control system 530 generally includes an x-ray controller 532, a table controller 534, a gantry controller 536, and a data acquisition system 538. The x-ray controller 532 provides power and timing signals to the x-ray source 504 and the gantry controller 536 controls the rotational speed and position of the gantry 502. The table controller 534 controls a table 540 to position the subject 512 in the gantry 502 of the CT system 500.

The DAS 538 samples data from the detector elements 510 and converts the data to digital signals for subsequent processing. For instance, digitized x-ray data is communicated from the DAS 538 to the data store server 524. The image reconstruction system 526 then retrieves the x-ray data from the data store server 524 and reconstructs an image therefrom, as described above. The image reconstruction system 526 may include a commercially available computer processor, or may be a highly parallel computer architecture, such as a system that includes multiple-core processors and massively parallel, high-density computing devices. Optionally, image reconstruction can also be performed on the processor 522 in the operator workstation 516. Reconstructed images can then be communicated back to the data store server 524 for storage or to the operator workstation 516 to be displayed to the operator or clinician.

The CT system 500 may also include one or more networked workstations 542. By way of example, a networked workstation 542 may include a display 544; one or more input devices 546, such as a keyboard and mouse; and a processor 548. The networked workstation 542 may be located within the same facility as the operator workstation 516, or in a different facility, such as a different healthcare institution or clinic.

The networked workstation 542, whether within the same facility or in a different facility as the operator workstation 516, may gain remote access to the data store server 524 and/or the image reconstruction system 526 via the communication system 528. Accordingly, multiple networked workstations 542 may have access to the data store server 524 and/or image reconstruction system 526. In this manner, x-ray data, reconstructed images, or other data may be exchanged between the data store server 524, the image reconstruction system 526, and the networked workstations 542, such that the data or images may be remotely processed by a networked workstation 542. This data may be exchanged in any suitable format, such as in accordance with the transmission control protocol ("TCP"), the internet protocol ("IP"), or other known or suitable protocols.

Figure 6:
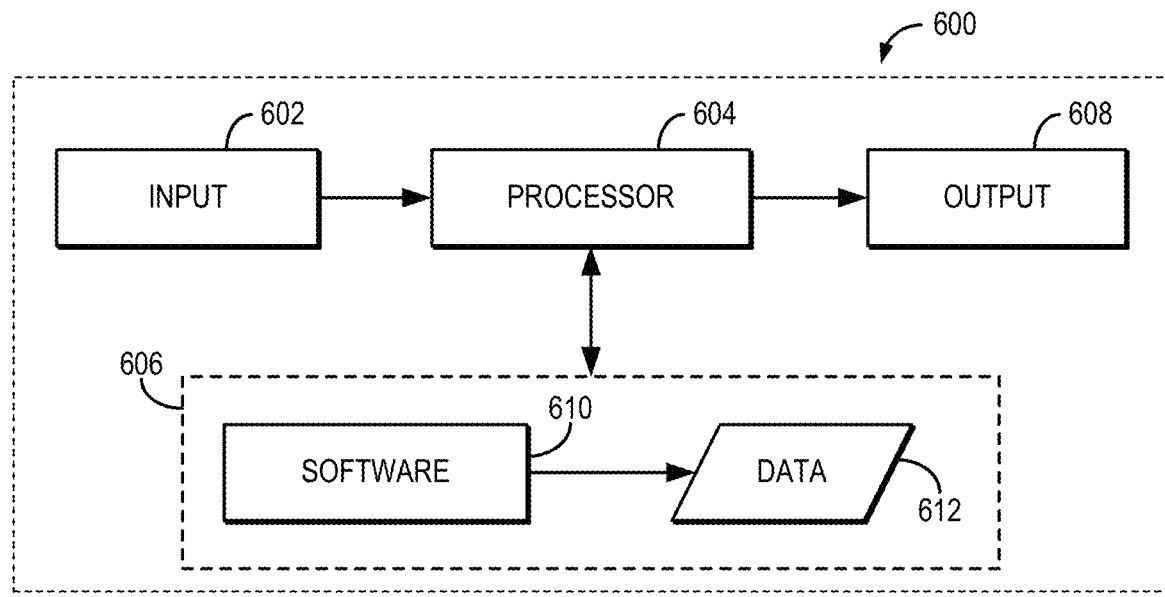
FIG. 6 is a block diagram of an example computer system that can implement methods described in the present disclosure.

Referring now to FIG. 6, a block diagram of an example of a computer system 600 that can preprocess x-ray measurement data and reconstruct images therefrom according to embodiments described in the present disclosure is shown. Additionally or alternatively, the computer system 600 can also be used to control the operation of the on-board kV and MV imagers in an EBRT system in order to acquire x-ray measurement data. The computer system 600 generally includes an input 602, at least one hardware processor 604, a memory 606, and an output 608. Thus, the computer system 600 is generally implemented with a hardware processor 604 and a memory 606.

In some embodiments, the computer system 600 can be a workstation, a notebook computer, a tablet device, a mobile device, a multimedia device, a network server, a mainframe, one or more controllers, one or more microcontrollers, radiation treatment planning system ("TPS"), or any other general-purpose or application-specific computing device.

The computer system 600 may operate autonomously or semi-autonomously, or may read executable software instructions from the memory 606 or a computer-readable medium (e.g., a hard drive, a CD-ROM, flash memory), or may receive instructions via the input 602 from a user, or any another source logically connected to a computer or device, such as another networked computer or server. Thus, in some embodiments, the computer system 600 can also include any suitable device for reading computer-readable storage media.

In general, the computer system 600 is programmed or otherwise configured to implement the methods and algorithms described in the present disclosure. For instance, the computer system 600 can be programmed to generate monoenergetic projection data from first and second x-ray measurement data as described above, to reconstruct images from monoenergetic projection data, or combinations thereof.

The input 602 may take any suitable shape or form, as desired, for operation of the computer system 600, including the ability for selecting, entering, or otherwise specifying parameters consistent with performing tasks, processing data, or operating the computer system 600. In some aspects, the input 602 may be configured to receive data, such as first and/or second x-ray measurement data, radiation treatment plans, and so on. Such data may be processed as described above to generate monoenergetic projection data from first and second x-ray measurement data as described above, to reconstruct images from monoenergetic projection data, or combinations thereof. In addition, the input 602 may also be configured to receive any other data or information considered useful for implementing the methods described above.

Among the processing tasks for operating the computer system 600, the one or more hardware processors 604 may also be configured to carry out any number of post-processing steps on data received by way of the input 602.

The memory 606 may contain software 610 and data 612, such as data acquired with a medical image system or previously generated radiation treatment plans, and may be configured for storage and retrieval of processed information, instructions, and data to be processed by the one or more hardware processors 604. In some aspects, the software 610 may contain instructions directed to implementing the methods described above.

In addition, the output 608 may take any shape or form, as desired, and may be configured for displaying medical images, radiation treatment plans, and other data computed, derived, or otherwise obtained from such images or plans, in addition to other desired information.

Figure 7:
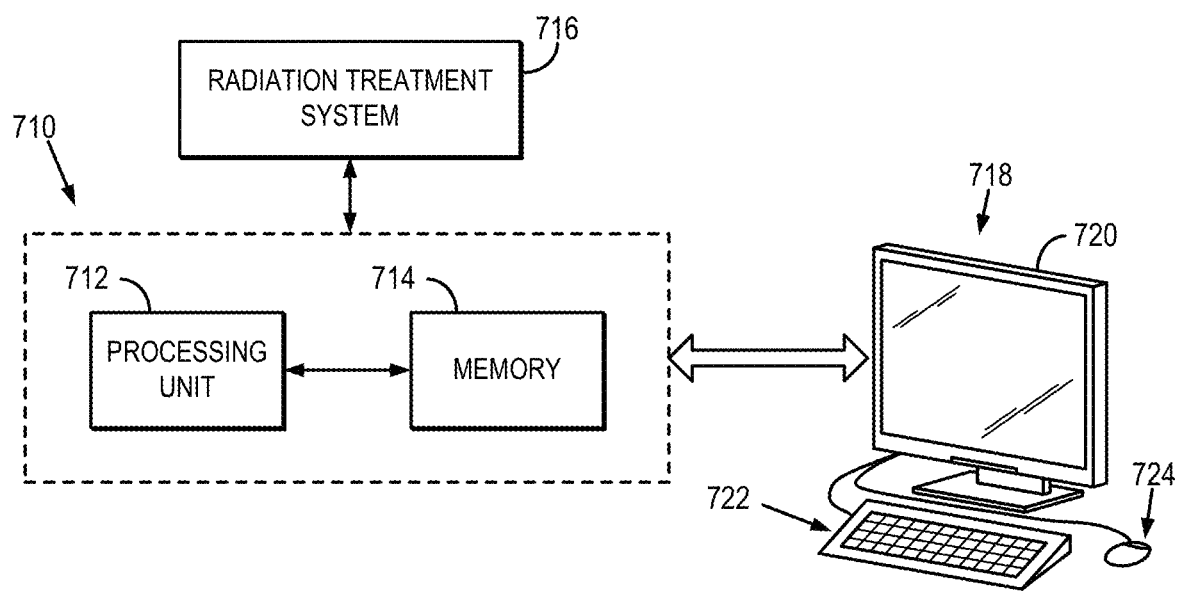
FIG. 7 is a block diagram illustrating an example radiation treatment planning system, which can generate and/or update a radiation treatment plan based on the methods described in the present disclosure.

As noted, the systems and methods described in the present disclosure can be implemented using a radiation treatment planning system. Referring now to FIG. 7, an example of such a radiation treatment planning system 710 is illustrated. The radiation treatment planning system 710 is preferably in communication with one or more radiation treatment systems 712, which may include any suitable radiation treatment system.

The radiation treatment planning system 710 generally includes a memory 714 that is operably coupled to a processor unit 716. As an example, the processor unit 716 can be a commercially available computer processor, such as those described above. The processor unit 716 is configured to carry out one or more of the steps of the methods described above.

As an example, the memory 714 can include a plurality of memory elements, or can include a single memory element. In general, the memory 714 is configured to store information regarding patient data, a treatment target (e.g., a tumor located within a patient), imaging beam model data, treatment beam model data, dose matrices, and so on.

Preferably, the radiation treatment planning system 710 includes, or is otherwise in communication with, a user interface 718. As an example, the user interface 718 provides information to a user, such as a medical physicist. For example, the user interface 718 can include a display 720 and one or more input devices, such as a keyboard 722 and mouse 724.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. An imaging system, comprising:
   a gantry that is rotatably coupled to a drive stand and is configured to rotate through an imaging arc about a bore;
   a first x-ray source mounted on the gantry and configured to direct x-rays of a first beam energy through a peripheral portion of a target volume disposed in the bore and toward a first x-ray detector mounted on the gantry laterally offset from the center of the target volume;
   a second x-ray source mounted on the gantry angularly offset from the first x-ray source and configured to direct x-rays of a second beam energy higher than the first beam energy through a portion of the target volume including the center of the target volume and toward a second x-ray detector mounted on the gantry; and
   a processor configured to:
      cause the gantry to perform a rotation including an imaging arc;
      receive first x-ray measurement data from the first x-ray detector;

receive second x-ray measurement data from the second x-ray detector; and reconstruct an image of the target volume from the first and second x-ray measurement data, wherein the image has an extended field-of-view;

wherein the processor reconstructs the image from the first and second x-ray measurement data by:

applying a mono-energizing transform correction to the first and second x-ray measurement data, generating output as monoenergetic projection data; and reconstructing the image from the monoenergetic projection data.

2. The imaging system of claim 1, wherein the first x-ray beam energy is in a kilovolt (kV) range.

3. The imaging system of claim 1, wherein the second x-ray beam energy is in a megavolt (MV) range.

4. The imaging system of claim 1, wherein the second x-ray source comprises a linear accelerator (LINAC) source that is operable to generate a therapeutic radiation beam in addition to x-rays of the second beam energy.

5. The imaging system of claim 1, wherein the first x-ray source is configured to generate the first x-ray beam such that the first x-ray beam does not pass through the center of the target volume.

6. The imaging system of claim 1, wherein the reconstructed image is non-truncated.

7. The imaging system of claim 1, wherein the first x-ray source and the second x-ray source are arranged relative to each other such that the first x-ray beam and the second x-ray beam partially overlap.

8. The imaging system of claim 1, wherein the second x-ray detector comprises multiple scintillator and photodiode layers.

9. The imaging system of claim 8, wherein each scintillator layer is composed of $GdO_2S_2$:Tb.

10. The imaging system of claim 8, wherein each photodiode layer is composed of Si:H.

11. The imaging system of claim 1, wherein the first x-ray detector and second x-ray detector each have widths no greater than 43 cm.

12. The imaging system of claim 1, wherein reconstructing the image further includes applying an edge-preserving noise reduction algorithm to reduce noise in the image.

13. The imaging system of claim 1, wherein the mono-energizing transform correction comprises:

reducing noise in the first and second x-ray measurement data;

converting the first x-ray measurement data and the second x-ray measurement data to a common energy by modeling the target volume as a composition of a first material through which density projections can be pre-estimated from an approximate prior image reconstruction, and a second material whose density projections can be estimated by minimizing an objective function based in part on a poly-energetic beam model.

14. The imaging system of claim 13, wherein minimizing the objective function comprises minimizing a roughness penalized likelihood function.

15. The imaging system of claim 1, wherein the first and second x-ray sources are integrated into a cone-beam computed tomography system.

16. The imaging system of claim 1, wherein the processor determines three-dimensional (3D) dose maps from the first and second x-ray measurement data and provides the 3D dose maps to an adaptive radiotherapy treatment system.

17. A computer-implemented method of imaging in an imaging system that includes a gantry that is configured to rotate in an imaging arc about a bore, a first x-ray source mounted on the gantry and configured to direct x-rays of a first beam energy through a peripheral portion of a target volume disposed in the bore and toward a first x-ray detector mounted on the gantry laterally offset from the center of the target volume, and a second x-ray source mounted on the gantry angularly offset from the first x-ray source and configured to direct x-rays of a second beam energy higher than the first energy through a portion of the target volume including the center of the target volume and toward a second x-ray detector mounted on the gantry, the method comprising:

receiving first x-ray measurement data from the first x-ray detector while the gantry is rotating through the imaging arc;

receiving second x-ray measurement data from the second x-ray detector while the gantry is rotating through the imaging arc; and reconstructing an image of the target volume from the first and second x-ray measurement data using a computer system, wherein the image depicts an extended field-of-view region;

wherein reconstructing the image further comprises applying a mono-energizing transform correction and edge-preserving noise reduction algorithm to the first and second x-ray measurement data.

18. The method of claim 17 wherein the first x-ray beam is directed so as to not pass through the center of the target volume.

19. The method of claim 17, wherein the reconstructed image is non-truncated.

20. The method of claim 17, wherein the first x-ray beam and second x-ray beam are directed to partially overlap.

21. The method of claim 17, further comprising determining 3D dose maps from the first and second volumetric image data and providing the determined dose maps to an adaptive radiotherapy treatment system.

22. A method of reconstructing an image from x-ray measurement data, the method comprising:

(a) accessing first x-ray measurement data with a computer system, the first x-ray measurement data corresponding to a first x-ray beam having a first x-ray beam energy passing through a peripheral portion of a target volume along a beam axis that is laterally offset from a center of the target volume;

(b) accessing second x-ray measurement data with the computer system, the second x-ray measurement data corresponding to a second x-ray beam having a second x-ray beam energy higher than the first x-ray beam energy and passing through a portion of the target volume including the center of the target volume;

(c) converting the first x-ray measurement data and the second x-ray measurement data to monoenergetic projection data corresponding to a common x-ray beam energy using the computer system; and (d) reconstructing an image from the monoenergetic projection data with the computer system, wherein the image depicts an extended field-of-view of the target volume.

23. The method of claim 22, wherein converting the first x-ray measurement data and the second x-ray measurement data to monoenergetic projection data comprises modeling the target volume as a composition of a first material through which density projections can be pre-estimated from an approximate prior image reconstruction, and a second material whose density projections can be estimated by minimizing an objective function based in part on a poly-energetic beam model.

24. The method of claim 23, wherein minimizing the objective function comprises minimizing a roughness penalized likelihood function.

25. The method of claim 22, wherein converting the first x-ray measurement data and the second x-ray measurement data to the monoenergetic projection data comprises applying a mono-energizing transform correction to the first and second x-ray measurement data, generating output as the monoenergetic projection data.

26. The method of claim 25, wherein converting the first x-ray measurement data and the second x-ray measurement data to the monoenergetic projection data further includes applying an edge-preserving noise reduction algorithm to at least one of the first x-ray measurement data and the second x-ray measurement data.

* * * * *